United States Patent
Chang

(10) Patent No.: US 9,827,550 B2
(45) Date of Patent: Nov. 28, 2017

(54) METHOD OF MANUFACTURING ABSORBENT MATERIAL FROM BIRD FEATHER

(71) Applicant: KWONG LUNG ENTERPRISE CO., LTD., Taipei (TW)

(72) Inventor: Yu-Shin Chang, Taipei (TW)

(73) Assignee: KWONG LUNG ENTERPRISE CO., LTD., Taipei (TW)

(*) Notice: Subject to any disclaimer, the term of this patent is extended or adjusted under 35 U.S.C. 154(b) by 315 days.

(21) Appl. No.: 14/570,323

(22) Filed: Dec. 15, 2014

(65) Prior Publication Data

US 2016/0167014 A1    Jun. 16, 2016

(51) Int. Cl.

| | |
|---|---|
| *B01J 20/32* | (2006.01) |
| *B01J 20/22* | (2006.01) |
| *A61L 9/013* | (2006.01) |
| *B01J 20/26* | (2006.01) |
| *B01J 20/28* | (2006.01) |
| *B01J 20/30* | (2006.01) |
| *B01D 15/08* | (2006.01) |
| *B01D 53/02* | (2006.01) |

(52) U.S. Cl.
CPC .............. *B01J 20/22* (2013.01); *A61L 9/013* (2013.01); *B01D 15/08* (2013.01); *B01D 53/02* (2013.01); *B01J 20/261* (2013.01); *B01J 20/262* (2013.01); *B01J 20/28004* (2013.01); *B01J 20/3021* (2013.01); *B01J 20/3078* (2013.01); *B01D 2257/708* (2013.01); *B01D 2257/90* (2013.01)

(58) Field of Classification Search
CPC ................................. B01J 20/32; B01D 53/02
USPC .......................................................... 502/401
See application file for complete search history.

(56) References Cited

FOREIGN PATENT DOCUMENTS

| | | |
|---|---|---|
| CN | 1439768 A | 9/2003 |
| CN | 101942742 A | 1/2011 |

OTHER PUBLICATIONS

Taiwan Patent Office, Office Action, Patent Application Serial No. TW103141700, Sep. 14, 2015, Taiwan.

*Primary Examiner* — Edward Johnson
(74) *Attorney, Agent, or Firm* — Rabin & Berdo, P.C.

(57) ABSTRACT

A method of manufacturing absorbent material from bird feather includes the steps of selecting an appropriate feather material, perform a pre-treatment for cleaning and sterilizing the feather material, crushing the feather material into a crushed material of a size of 0.1 um~1 cm, and performing a modification treatment of the crushed material by surface activation to produce an absorbent material. After the crushed feather material is processed by a modification treatment, the material may be used to manufacture an absorbent material having both deodoring and filtering functions for adsorbing metal ions, organic solvents, grease or volatile gases.

8 Claims, 2 Drawing Sheets

METHOD OF MANUFACTURING ABSORBENT MATERIAL FROM BIRD FEATHER

FIELD OF THE INVENTION

The present invention relates to the treatment and application of feather waste, in particular to a method and use of an absorbent material made from bird feather.

BACKGROUND OF THE INVENTION

Most of the downs used for making conventional down products are comprised of down and feather, wherein down is a feather fiber excluding any feather shafts and primary used as a thermal insulating material, and feather is a small feather containing feather shafts for providing a fluffy effect to the down. In summation, the down products containing both down and feather have the light, soft and warm features.

In addition, the small feather used in the down products primarily includes waterbird feathers (duck and goose feathers) with a length below 6 cm. Since duck and goose feathers are not of the same length and their length varies from 1 cm to 15 cm, therefore the duck and goose feather waste with the length below 6 cm has no economic value to down manufacturers anymore, and the quantity of such feather waste is huge. Manufacturers may produce feather powder from these feather wastes by hydrolysis, and the feather powder may be used as feed or fertilizer. However, the duck and goose feathers are full of keratin and disulfide bonds, and if the feather waste has not been hydrolyzed completely, the feed so produced cannot be digested by animals. Therefore, the duck and goose feather waste is a burden to down manufacturers, regardless of its disposal or reuse.

In view of the aforementioned problems and based on the basic biomaterial researches related to the application of degenerating and reconstructing feather and hair materials and conducted in the last century, finding a method of reusing the duck and goose feather waste and manufacturing a by-product to improve the economic benefit has been a long-standing issue to down manufacturers.

SUMMARY OF THE INVENTION

Therefore, it is a primary objective of the present invention to provide a method of manufacturing an absorbent material made from bird feather and an application of the absorbent material, wherein a selected feather waste is used to produce a by-product to achieve the effects of improving economic value, reducing unnecessary waste of materials, and lowering the production cost of the down products.

To achieve the aforementioned and other objectives, the present invention provides a method of manufacturing absorbent material from bird feather, comprising the steps of: selecting a feather material; performing a pre-treatment including the processes of cleaning, degreasing, drying and sterilizing the feather material; crushing the pre-treated feather material to form a crushed material with a size falling within a range of 0.1 um~1 cm; and finally performing a modification treatment of the crushed material to produce an absorbent material capable of absorbing a predetermined substance.

The bird feather is a leaf-shaped fiber, and tens of thousands tiny pores (20) are distributed densely on the feather shaft (10) (as shown in FIGS. 1 to 3) and have the features of absorbing substances. After the crushing treatment, a plurality of tiny debris or particles are produced to increase the specific surface area and improve the activity of molecules, so as to enhance the absorption function, and thus the product so produced can be used as an absorbent material, or used to manufacture filters for the deodoring and filtering purpose or adsorbing or filtering predetermined molecules in gas, liquid or solid. For example, the absorbent material can be used for filtering relatively larger suspended particles (with a size greater than 0.4 um) in water, or filtering pigments in water. The ground feather material after being processed by an appropriate surface modification treatment may be used for absorbing metal ions (such as copper, lead, zinc, chromium, magnesium, calcium, and arsenic ions), organic solvents (such as phenols and dyes) or volatile gases or grease (such as formaldehyde, ammonia, benzene, acetic acid, and hydrogen sulfide).

Preferably, the feather material is a bird feather with feather shafts, and the feather material may be selected from waterbird feathers (duck feathers or goose feathers) with a length greater than 1 cm. Of course, it may be a duck and goose feather waste with a length greater than 6 cm~15 cm but it cannot be used as a down filling material.

Preferably, the pre-treatment comprises a washing and degreasing process and a drying and sterilizing process, for removing the original smell of the animal feather, and the grease and bacteria attached on surfaces of the feather. In the washing and degreasing process, a surface activator with a weight equal to 4~10% of the weight of the feather is used to produce an aqueous solution, or an alkaline aqueous solution with a pH value of 7~10 is used for rinsing the feather at a temperature of 25° C.~90° C. for 0.5~2 hours, and then the feather is dehydrated after the rinsing takes place. In the drying and sterilizing process, high temperature drying and sterilization takes place at a temperature of 110° C.~140° C.

Preferably, the crushing treatment includes a low-level crushing, a mid-level crushing, a high-level crushing, or a combination of the above. Since feather comes with a specific tenacity, the feather material can be sheared and crushed directly into a crushed material (crushed down) with an average particle size below 1 cm in the low-level crushing. In the mid-level crushing, the tenacity of the feather is reduced and the brittleness of the feather is increased after performing a low-temperature ultrafine crushing process in a low-temperature environment of −30° C.~−120° C., and thus the fracture surface of the manufactured feather is smooth and even, and the pores are exposed from the feather shaft, wherein the feather material may be crushed by ball milling, air current, or shearing and then selected, so that the crushed material has an average particle size of 0.1 um~400 um. In the high-level crushing, the feather material is dissolved and granulated to extract keratin and form a crushed material with an average particle size of 0.1 um~10 um.

Preferably, the modification treatment of the crushed material may be achieved by using an activating agent to perform a surface activation, or performing a thermoplastic process with an accessory material, or combining to form a composite material.

The activating agent is one selected from the group consisting of an oxygen-containing oxidizer, a sulfur-containing reducer, an acidic additive for acid treatment, an alkaline additive for alkali treatment, urea, an epoxide, and ethylenediamine, and the accessory material is one selected from the group consisting of hot-melt fiber, polyurethane, polyvinyl alcohol, polyvinyl chloride, polyethylene, polypropylene, polymethylmethacrylate, glycerol or diethylene glycol.

DESCRIPTION OF THE PREFERRED EMBODIMENTS

The present invention will become clearer in light of the following detailed description of an illustrative embodiment of this invention described in connection with the drawings. It is intended that the embodiments and drawings disclosed herein are to be considered illustrative rather than restrictive.

Figure 1:
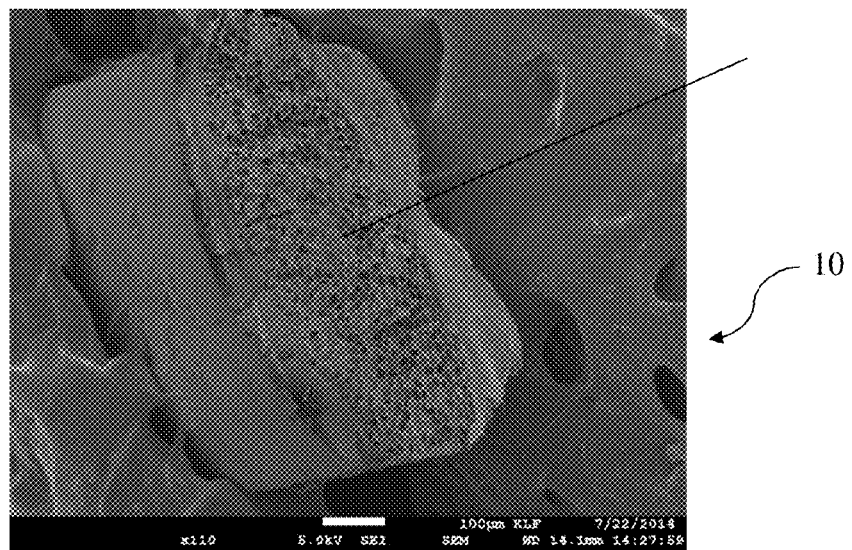
FIG. 1 is a cross-sectional view of a feather shaft observed from a microscope.
Figure 2:
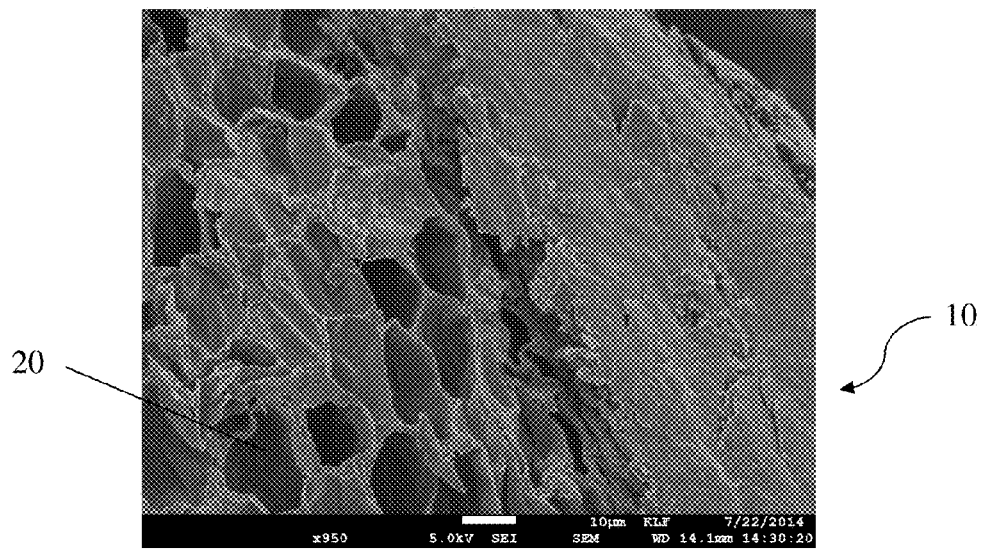
FIG. 2 is a schematic view of a feather shaft having irregular pores observed from a microscope.
Figure 3:
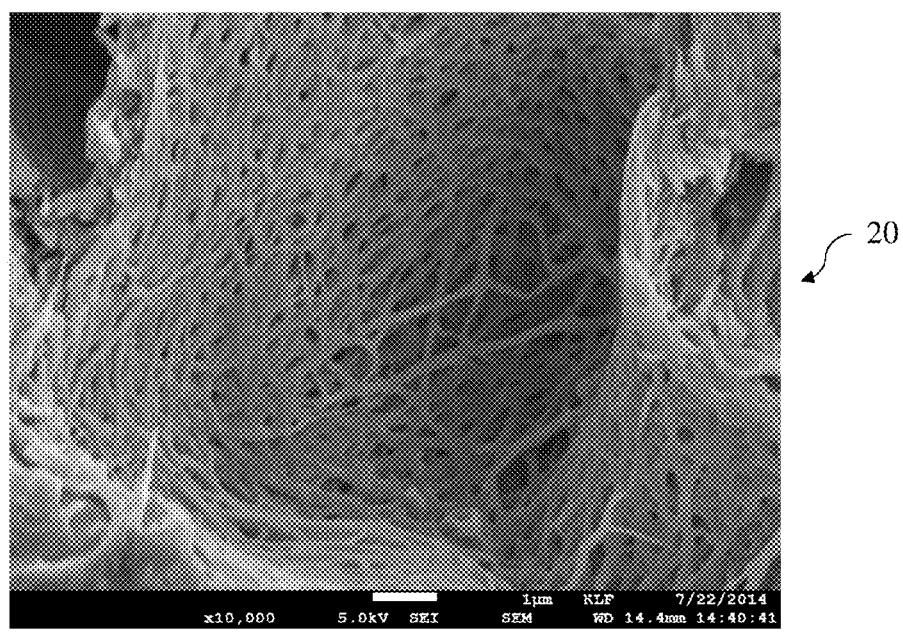
FIG. 3 is a schematic view of a pore having a mesh pore tissue as its pore wall observed from a microscope.

Bird feather such as waterbird feather, or goose or duck feather primarily used as a down material comes with different lengths ranging from 1 cm to 15 cm. With reference to FIGS. 1 to 3 for the cross-section of the structure of a feather shaft 10 observed from a microscope with ×110, ×950, ×10000 respectively, tens of thousands tiny pores 20 are distributed densely in the feather shaft 10, and the surface of the feather is modified and activated according to different application fields, so that the feather material can be used for absorbing molecules of different substances.

The feather shaft 10 may be crushed to different sizes within a range of 0.1 um~1 cm by physical and mechanical methods and different sizes provide different specific surface areas. The larger the specific surface area, the more active the molecules, and the larger quantity the absorbed substance. After the feather is crushed, the surface of the crushed feather is modified and activated according to the polarity of the absorbed substance, and the absorbent material may be used for absorbing or filtering molecules of a gas, liquid or solid.

In an embodiment of the present invention, the feather material is a duck feather or goose feather with feather shafts 10, and the feather has a length falling within a range of 1~15 cm. After the feather material with a length above 6~15 cm is selected as a down material, the remaining feather is the feather waste. Firstly, a manufacturing process (which is a pre-treatment) of the feather is required, and the pre-treatment provided for removing impurities including the smell, grease and bacteria of the animal feather comprises a washing and degreasing process and/or a drying and sterilizing process. After the feather material is selected, the washing and degreasing process of the selected feather material takes place, wherein a surface activator with a weight approximately equal to 4~10% of the feather material is used to produce an aqueous solution, or an alkaline aqueous solution with a pH value of 7~10 is used for washing the feather material at a temperature of 25° C.~90° C. for 0.5~2 hours. The feather material is dehydrated after being washed, and then the drying and sterilizing process takes place, wherein the dehydrated feather material is placed in a high temperature environment of 110° C.~140° C. for the sterilization while drying and sterilizing the feather material continuously for at least 20~40 minutes. Until the down material is dried completely, the manufacturing process of the pre-treatment is completed.

After the pre-treatment, the crushing treatment takes place. In the crushing treatment, the feather material is crushed into a crushed material with a size of 0.1 um~1 cm in order to increase the specific surface area of the feather material and improve the adsorptability of the pores on the surface of the feather material. In an embodiment of the present invention, the crushing treatment of the feather material includes a low-level crushing which shears the feather material directly, a mid-level crushing which crushes the feather material to an ultrafine level in a low-temperature environment, and a high-level crushing which dissolves and granulate the feather material to form the crushed material.

Since feather has a specific tenacity, the feather material can be sheared and manufactured to form a crushed material (or crushed down) with a length below 1 cm by the low-level crushing, and the mid-level crushing and high-level crushing may be used together as needed to obtain a crushed material with finer particles.

In the mid-level crushing, the low-temperature environment reduces the tenacity of the feather material, so that the brittleness of the feather material is increased, and the fracture surface of the manufactured feather material is smooth and even, and the pores of the feather material are exposed from the surface of the feather material to enhance the absorption. In this embodiment, the mid-level crushing is adopted to process the feather material or the low-level crushing is adopted and processed by putting the feather material into a low-temperature environment of −30° C. to −120° C. and crushing the feather material by ball milling, air current or shearing to form a crushed material with a particle size of 0.1 um~400 um.

In the high-level crushing, the feather material is dissolved and granulated, and then the keratin particles are extracted to form a crushed material with an average particle size of 0.1 um~10 um. In the extraction of the keratin particles, different extraction methods may be used according to the purity of the keratin. This embodiment may adopt the following two methods:

1. Add 0.5M sodium sulfide (inorganic salt) solution to the feather material or the crushed material processed by the low-level crushing, and then heat the material up to 30° C., and finally stir and dissolve the feather material (or the crushed material) in the solution and collect a supernatant by using a filter paper. Slowly pour the ammonium sulfide solution into the supernatant (with a volume ratio of 1:1), and collect the precipitated product, and rinse the precipitate by clean water for several times before dissolving the precipitate back into the sodium hydroxide solution, so as to obtain the purified protein particles.

2. Use 5% of 2-hydroxy-1-ethanethiol (or thioglycol, which is a reducer) as a solvent and add the solvent into 2.6M of thourea and 5M of urea to produce a solution, and then stir the feather material or the crushed material processed by the low-level crushing with the solution, and add Tris-HCl in an alkaline environment (with a pH value of 8.5) to precipitate the keratin, and centrifuge and filter the keratin to obtain keratin particles.

After the crushing treatment, the surface modification treatment takes place to produce an absorbent material used for manufacturing various different types of filters. In an embodiment of the present invention embodiment, the following two modification treatment methods may be used.

1. Use an activating agent to activate the surface of the crushed material.

2. Use an accessory material to combine with the crushed material to form a composite material. After the surface is activated and modified, the material may be applied in a filter for adsorbing metal ions, organic solvents, grease or volatile gases. The modification treatment process of the feasible embodiments of the present invention and its application are described below:

(1) The crushed material with an average size of 0.1 um~400 um is mixed and hot melted with an accessory material in a weight proportion of 1:1 to form a non-woven cloth which can be used as a filter for absorbing harmful ions of a heavy metal (such as copper ions) in wastewater or sewage at room temperature of 20~60° C.

(2) An activating agent $Na_2S_2O_5$ is used to perform a surface activation of a crushed material with an average size of 0.1 um~400 um to enhance the adsorptability of the $Pb^{2+}$ ions and hot melt the crushed material with polypropylene (PP) to form a filter for absorbing metal ions in water.

(3) Since keratin particles have the property of interacting with the metal ions, the crushed material (or keratin particles) with an average size of 0.1 um~10 um is mixed with an accessory material (polyurethane) to produce a porous film capable of absorbing the metal ions effectively, the porous film has a significant and the adsorptability when it is used in water with a pH value of 1.5~2.5.

(4) The crushed material with a size of approximately 1 cm is used as a main material and an appropriate accessory material is added to produce a filter, and the crushed material may be used for adsorbing a non-water soluble organic solvent, and may form a gel quickly with the crushed material. In addition, the solvent and the crushed material can be separated by centrifugation or compression, so that the filter may be used repeatedly.

(5) The crushed material with a size of approximately 400 um~1 cm is used as a main material and an appropriate accessory material is added to produce a filter for filtering suspended impurities and particles with a size greater than 0.4 um in filtered water and pigments in the water.

(6) The crushed material with a size of approximately 1 cm is used as a main material, and hydrogen peroxide is used as an activating agent, so that the crushed material can be used for absorbing phenols in an aqueous solution. At least 70% of the phenols in the water with a pH value of 2~3 can be absorbed at room temperature of approximately 30° C. in a day.

(7) The crushed material with a size of approximately 1 cm is used as a main material, and hydrophilic and lipophilic groups existed in the feather shafts and the hollow porous structure of the feather shafts are mixed with an accessory material (polypropylene and polyvinyl chloride) to produce a fabric for absorbing greases attached on water surface.

(8) The crushed material with a size of 0.1 um~1 cm is used. Since this crushed material has relatively larger specific surface area and higher hydrophilic and organphilic characteristics, these characteristics are conducive to the adsorption of volatile organic compound (VOC). After the surface activation of the crushed material is performed by using an activating agent such as citric acid, ferrous sulfate, copper sulfate, or sulfonated cobalt phthalocyanine, the crushed material may be used to produce a functional formaldehyde absorbent material, a functional ammonia absorbent material or a functional benzene absorbent material.

(9) The crushed material with a size of approximately 400 um~1 cm is used and added into 0.1 mol/L of NaOH solution, and an activating agent such as ethylenediamine or epichlorohydrin is added and reacted for 2 hours, and then neutralized by an acid, so that the crushed material may be used for adsorbing chromium ions.

(10) The crushed material with a size of approximately 400 um~1 cm is used and processed by an activating agent such as nitric acid or acetic acid, and some of the amines of the keratin are cationized and capable of adsorbing anions such as chromium ions or having an electrostatic interaction with cations to provide a chemical adsorption.

In summation of the description above, the present invention improves over the prior art, and is thus duly filed for patent application. While the invention has been described by means of specific embodiments, numerous modifications and variations could be made thereto by those skilled in the art without departing from the scope and spirit of the invention set forth in the claims.

What is claimed is:

1. A method of manufacturing absorbent material from bird feather, comprising the steps of:
    selecting a feather material;
    performing a pre-treatment for cleaning and sterilizing the feather material;
    crushing the pre-treated feather material to form a crushed material with a size falling within a range of 0.1 um~1 cm; and
    performing a modification treatment of the crushed material to produce an absorbent material capable of absorbing a predetermined substance.

2. The method of manufacturing absorbent material from bird feather as claimed in claim 1, wherein the pre-treatment includes a washing and degreasing process and/or a drying and sterilizing process.

3. The method of manufacturing absorbent material from bird feather as claimed in claim 1, wherein the feather material is a bird feather with feather shafts.

4. The method of manufacturing absorbent material from bird feather as claimed in claim 3, wherein the feather material is one selected from a group consisting of duck feather and goose feather with a length over 1 cm.

5. The method of manufacturing absorbent material from bird feather as claimed in claim 1, wherein the feather material is ground by low-level crushing, mid-level crushing, high level crushing or any combination of the above, and the low-level crushing directly shears and crushes the feather material into a crushed material with an average particle size below 1 cm, and the mid-level crushing crushes the feather material into a ultrafine crushed material with an average particle size within a range of 0.1 um~400 um in a low-temperature environment of −30° C. to −120° C. by ball milling, air current, or shearing, and the high level crushing dissolves and granulates the feather material to form a crushed material with an average particle size within a range of 0.1 um~10 um.

6. The method of manufacturing absorbent material from bird feather as claimed in claim 1, wherein the modification treatment of the crushed material includes a step of performing a surface activation of an activating agent, or performing a thermoplastic process of an accessory material, or combining to form a composite material.

7. The method of manufacturing absorbent material from bird feather as claimed in claim 6, wherein the activating agent is one selected from the group consisting of an oxygen-containing oxidizer, a sulfur-containing reducer, an acidic additive for acid treatment, an alkaline additive for alkali treatment, urea, an epoxide, and ethylenediamine.

8. The method of manufacturing absorbent material from bird feather as claimed in claim 6, wherein the accessory material is one selected from the group consisting of hot-melt fiber, polyurethane, polyvinyl alcohol, polyvinyl chloride, polyethylene, polypropylene, polymethylmethacrylate, glycerol and diethylene glycol.

\* \* \* \* \*